(12) United States Patent
Jamruszka (10) Patent No.: US 8,216,840 B2
(45) Date of Patent: Jul. 10, 2012

(54) METHODS FOR STRATIFICATION AND STORAGE OF SOMATIC EMBRYOS

(75) Inventor: Amy M Jamruszka, Port Orchard, WA (US)

(73) Assignee: Weyerhauser NR Company, Federal Way, WA (US)

( * ) Notice: Subject to any disclaimer, the term of this patent is extended or adjusted under 35 U.S.C. 154(b) by 146 days.

(21) Appl. No.: 12/235,460

(22) Filed: Sep. 22, 2008

(65) Prior Publication Data

US 2009/0087908 A1    Apr. 2, 2009

Related U.S. Application Data

(60) Provisional application No. 60/975,717, filed on Sep. 27, 2007.

(51) Int. Cl.
| | |
|---|---|
| *C12N 5/00* | (2006.01) |
| *C12N 5/02* | (2006.01) |
| *A01H 11/00* | (2006.01) |
| *A01H 9/00* | (2006.01) |
| *A01H 5/00* | (2006.01) |

(52) U.S. Cl. ............... 435/422; 435/420; 435/430.1; 435/410; 800/295; 800/298

(58) Field of Classification Search ............... None
See application file for complete search history.

(56) References Cited

U.S. PATENT DOCUMENTS

| | | | |
|---|---|---|---|
| 5,563,061 | A | 10/1996 | Gupta |
| 2004/0072143 | A1 | 4/2004 | Timmis et al. |
| 2004/0096970 | A1 | 5/2004 | Gupta |
| 2004/0267457 | A1 | 12/2004 | Timmis et al. |

FOREIGN PATENT DOCUMENTS

| | | |
|---|---|---|
| AU | 2003231584 | 6/2004 |
| NZ | 534256 A | 3/2006 |

OTHER PUBLICATIONS

Raja Rao et al. Enhancement of Thiazopyr Bioefficacy by Inhibitors of Monooxygenases Pestic. Sci. 1995,45,209-213.*

Mauri, P V et al: "Effect of abscisic acid and stratification on somatic embryo maturation and germination of holm oak (*Quercus ilex* L.)" Invitro Cellular & Developmental Biology Plant, vol. 40, No. 5, Sep. 2004, pp. 495-498, XP009111538, ISSN: 1054-5476.

J. S. Taylor & P.F. Wareing, The effect of stratification on the endogenous levels of gibberellins and cytokinins in seeds of douglas-fir (*Pseudotsuga menziesii* (Mirb.) Franco) and sugar pine (*Pinus lamertiana* Dougl.), Department of Botany, University of Wales, Aberystwyth, U.K., Plant, Cell and Environment (1979) 2, 165-171.

Nagmani, R., et al., "Anatomical Comparison of Somatic and Zygotic Embryogeny in Conifers," in S.M. Jain et al.(eds.), vol. 1, Somatic Embryogenesis in Woody Plants, Series: Forestry Sciences, vol. 44, 1995, pp. 23-48.

* cited by examiner

*Primary Examiner* — Annette Para (74) *Attorney, Agent, or Firm* — Christensen O'Connor Johnson Kindness PLLC (57) ABSTRACT

In one aspect, a method is provided for producing stratified cotyledonary conifer somatic embryos. The method comprises (a) incubating a culture comprising immature conifer somatic embryos in a culture vessel comprising a development medium having an osmolality in the range of from 300 mM/Kg to 450 mM/Kg at a temperature of from 22° C. to 25° C. for a first incubation period sufficient in length for at least a portion of the embryos to reach anatomical maturity; and (b) subjecting the embryos in the culture vessel in accordance with step (a) to a temperature of from 0° C. to 10° C. for a second incubation period of at least one week to produce stratified cotyledonary somatic embryos.

7 Claims, 3 Drawing Sheets

METHODS FOR STRATIFICATION AND STORAGE OF SOMATIC EMBRYOS

FIELD OF THE INVENTION

The present invention relates to methods for producing plant embryos in vitro, and optionally producing plants from the plant embryos.

BACKGROUND

The demand for coniferous trees, such as pines and firs, to make wood products continues to increase. One proposed solution to this problem is to identify individual trees that possess desirable characteristics, such as a rapid rate of growth, and produce numerous, genetically identical clones of the superior trees by somatic cloning.

Somatic cloning is the process of creating genetically identical trees from tree tissue other than the male and female gametes. In one approach to somatic cloning, plant tissue is cultured in an initiation medium which includes hormones, such as auxins and/or cytokinins, that initiate formation of embryogenic cells that are capable of developing into somatic embryos. The embryogenic cells are then further cultured in a maintenance medium that promotes multiplication of the embryogenic cells to form pre-cotyledonary embryos (i.e., embryos that do not possess cotyledons). The multiplied embryogenic cells are then cultured in a development medium that promotes development of colyledonary somatic embryos which can, for example, be placed within artificial seeds and sown in the soil where they germinate to yield conifer seedlings. The seedlings can be transplanted to a growth site for subsequent growth and eventual harvesting to yield lumber, or wood-derived products.

There is a continuing need to improve the efficiency of somatic cloning of conifer embryos in order to increase production of cotyledonary somatic embryos that are capable of germinating to yield pine plants. Preferably, the conifer somatic embryos formed in vitro are physically and physiologically similar, or identical, to conifer zygotic embryos formed in vivo in conifer seeds. The present invention provides methods that address this need with respect to conifers of the genus *Pinis*.

SUMMARY

In one aspect, a method is provided for producing stratified cotyledonary conifer somatic embryos. The method comprises (a) incubating a culture comprising immature conifer somatic embryos in a culture vessel comprising a development medium having an osmolality in the range of from 300 mM/Kg to 450 mM/Kg at a temperature of from 22° C. to 25° C. for a first incubation period sufficient, in length for at least a portion of the embryos to reach anatomical maturity; and (b) subjecting the embryos in the culture vessel in accordance with step (a) to a temperature of from 0° C. to 10° C. for a second incubation period of at least 1 week to produce stratified cotyledonary somatic embryos.

In another aspect, a method is provided for producing cotyledonary somatic embryos. The method comprises (a) incubating a culture comprising pre-cotyledonary conifer somatic embryos in or on a first development medium for a first incubation period; (b) singulating a plurality of the embryos treated in accordance with step (a); (c) culturing the plurality of singulated cotyledonary conifer somatic embryos in a culture vessel comprising a development medium having an osmolality in the range of from 300 mM/Kg to 450 mM/Kg at a temperature of from 22° C. to 25° C. for a second incubation period sufficient in length for at least, a portion of the embryos to reach anatomical maturity; and (d) subjecting the embryos in the culture vessel in accordance with step (c) to a temperature of from 0° C. to 10° C. for a third incubation period of at least 1 week to produce stratified cotyledonary somatic embryos.

The methods of the present invention are useful for preparing mature, stratified conifer somatic embryos with increased germination frequency and vigor that can be further characterized, such as by genetic or biochemical means and/or can be germinated to produce conifers, if so desired. Thus, for example, the methods of the invention can be used to more efficiently produce clones of individual conifers that possess one or more desirable characteristics, such as a rapid growth rate or improved wood quality.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2 is a panel of photographs of germinants produced under treatment group 1 (control) conditions (FIGS. 2A-2C), or produced under treatment group 14 conditions (FIGS. 2D-2F), demonstrating the improved germinant vigor obtained using the conditions of treatment 14, as described in EXAMPLE 2;

DETAILED DESCRIPTION

Unless specifically defined herein, all terms used herein have the same meaning as they would to one skilled in the art of the present invention.

As used herein, the term "development stage" refers to the period during somatic cloning during which histogenesis and growth of tissues and organs occurs in art immature embryo to reach a full-sized mature embryo capable of germination into a plant.

As used herein, the term "immature embryo" refers to an embryo that is not yet capable of germination into a plant, and includes embryos in early stage development (i.e., pre-cotyledonary embryos), and mid-stage development (i.e., embryos with cotyledons or hypocotyls that are not yet fully developed).

As used herein, the term "anatomical maturity" refers to an embryo that possesses developed cotyledons and hypocotyl.

As used herein, the term "cotyledonary embryo" refers to an embryo with a well-defined, elongated bipolar structure with latent meristematic centers having one or more clearly visible cotyledonary primordia at one end and a latent radicle at the opposite end.

As used herein, the term "pre-cotyledonary embryo" refers to an embryo that does not yet have cotyledons.

As used herein, the term "normal germinant" denotes the presence of all expected parts of a plant at time of evaluation. The expected parts of a plant may include a radicle, a hypocotyl, one or more cotyledon(s), and an epicotyl. In the case of gymnosperms, a normal germinant is characterized by the radicle having a length greater than 3 mm and no visibly discernable malformations compared to the appearance of embryos germinated from natural seed.

As used herein, the term "radicle" refers to the part of a plant embryo that develops into the primary root of the resulting plant.

As used herein, the term "hypocotyl" refers to the portion of a plant embryo or seedling located below the cotyledons but above the radicle.

As used herein, the term "epicotyl" refers to the portion of the seedling stem that is above the cotyledons.

As used herein, the term "embryonal suspensor mass" or "ESM" refers to a cell mass plated onto the surface of nutrient medium contained either in a semi-solid gel or as a liquid in a porous matrix capable of providing physical support, and left to grow for a period up to three months. During the three-month incubation time, somatic embryos grow from microscopic precursor cell groups into visible early-stage embryos and eventually to anatomically mature embryos. The structure of the ESM after several weeks of incubation typically consists of a proliferated mat with a few embryos sitting in direct contact with media, but most embryos forming on the top or side of the still proliferating cell mass.

As used herein, the term "stratification" refers to subjecting embryos to a cold treatment (e.g., 0° C. to 10° C.) prior to germination. Stratification (moist chilling) is a treatment used for overcoming germination resistance in the seeds of many temperate species (Taylor & Waring, *Plant, Cell, And Environment* 2:165-171, 1979).

Unless stated otherwise, all concentration values that are expressed as percentages are weight per volume percentages.

In accordance with the methods of die invention, it has been unexpectedly discovered that culturing immature conifer somatic embryos in or on a development medium comprising an osmolality in the range of from 300 mM/kg to 450 mM/kg for a first incubation period, followed by culturing the embryos on the same development media at a temperature from 0° C. to 10° C. for a second incubation period, produces embryos with increased germination frequency and vigor in comparison to embryos that are incubated in development medium and then transferred to a stratification medium that has an osmolality of less than 150 mM/kg and subjected to cold treatment (stratification), as described in EXAMPLES 2-4. In addition to improved germination frequency and germinant vigor, the omission of the media transfer step between development and stratification provides several other advantages, including simplified production of cotyledonary embryos, and optional cold storage of embryos on development media prior to germination, thereby allowing flexibility in the timing and use of the embryos. For example, the methods of the invention allow for the accumulation and synchronization of embryo populations prior to field testing.

In accordance with the foregoing, in one aspect, a method is provided for producing stratified cotyledonary conifer somatic embryos. The method comprises (a) incubating a culture comprising immature conifer somatic embryos in a culture vessel comprising a development medium having an osmolality in the range of from 300 mM/Kg to 450 mM/Kg at a temperature of from 22° C. to 25° C. for a first incubation period sufficient in length for at least a portion of the embryos to reach anatomical maturity; and (b) subjecting the embryos in the culture vessel in accordance with step (a) to a temperature of from 0° C. to 10° C. for a second incubation period of at least 1 week to produce stratified cotyledonary somatic embryos.

The methods of the invention can be used to produce cotyledonary somatic embryos from any conifer, such as members of the genus *Pinus*, such as *Loblolly* pine (*Pinus taedti*) and *Radiata* pine. Again, by way of example, Douglas fir embryos can be produced by the methods of the invention.

A population of mature conifer somatic embryos produced according to the methods of the invention has a greater efficiency of germinating into conifer plants than a population of conifer somatic embryos produced according to an otherwise identical control method that includes the post-development step of transferring embryos from development media having an osmolality in the range of from 300 mM/Kg to 450 mM/Kg to a stratification media having an osmolality of less than 150 mM/kg.

In accordance with the methods of the invention, prior to stratification, a culture comprising immature conifer somatic embryos, such as embryonal suspensor cell masses (ESM), is incubated in a development medium that promotes the development of cotyledonary embryos for a first incubation period.

Immature conifer somatic embryos, such as, for example, pre-cotyledonary conifer somatic embryos, can be prepared from conifer somatic cells, such as cells obtained from conifer embryos. For example, cells from conifer embryos can be induced by hormones to form embryonal suspensor cell masses (ESMs) that can be treated in accordance with the present invention to yield mature conifer somatic embryos. ESMs can be prepared, for example, from pre-cotyledonary embryos removed from seed. For example, the seed are surface sterilized before removing the pre-cotyledonary embryos, which are then cultured on, or in, an induction medium that permits formation of ESMs which include early state embryos in the process of multiplication by budding and cleavage. ESMs are typically cultured in a maintenance medium to form pre-cotyledonary somatic embryos. Non-limiting examples of ESM culture conditions and suitable induction and maintenance media are further described below.

Induction

Thus, in some embodiments, conifer somatic cells are cultured in, or on, an induction medium to yield embryogenic cells. Embryogenic cells are cells that are capable of producing one or more cotyledonary conifer somatic embryos and include, for example, conifer embryonal suspensor masses. The induction medium typically includes inorganic salts and organic nutrient materials. The osmolality of the induction medium is typically about 160 mg/kg or even lower, but it may be as high as 170 mM/kg. The induction medium typically includes growth hormones. Examples of hormones that can be included in the induction medium are auxins (e.g., 2,4-dichlorophenoxyacetic acid (2,4-D)) and cytokinins (e.g., 6-benzylaminopurine (BAP)). Auxins can be utilized, for example, at a concentration of from 1 mg/L to 200 mg/L. Cytokinins can be utilized, for example, at a concentration of from 0.1 mg/L to 10 mg/L.

The induction medium may contain an absorbent composition, especially when very high levels of growth hormones are used. The absorbent composition can be any composition that is not toxic to the embryogenic cells at the concentrations utilized in the practice of the present methods, and that is capable of absorbing growth-promoting hormones, and toxic compounds produced by the plant cells during embryo development that are present in the medium. Non-limiting examples of useful absorbent compositions include activated charcoal, soluble poly(vinyl pyrrolidone), insoluble poly(vinyl pyrrolidone), activated alumina, and silica gel. The absorbent composition may be present, in an amount, for example, of from about 0.1 g/L to about 5 g/L. An example of an induction medium useful in the practice of the present invention is medium $BM_1$ set forth in EXAMPLE 1 herein. The induction medium is typically solid, and may be solidified by inclusion of a gelling agent.

Conifer somatic cells are typically cultured in, or on, an induction medium for a period of from 3 weeks to 10 weeks, such as from 6 weeks to 8 weeks, at a temperature of from 10° C. to 30° C., such as from 15° C. to 25° C., or such as from 20° C. to 23° C.

Maintenance

The maintenance medium may be a solid medium, or it may be a liquid medium which can be agitated to promote growth and multiplication of the embryogenic tissue. The osmolality of (he maintenance medium is typically higher than the osmolality of the induction medium, typically in the range of 180-400 mM/kg. The maintenance medium may contain nutrients that sustain the embryogenic tissue, and may include hormones, such as one or more auxins and/or cytokinins, that promote cell division and growth of the embryogenic tissue. Typically, the concentrations of hormones in the maintenance medium is lower than their concentration in the induction medium.

It is generally desirable, though not essential, to include maltose as the sole, or principal, metabolizable sugar source in the maintenance medium. Examples of useful maltose concentrations are within the range of from about 1% to about 2.5%. An example of a suitable maintenance medium is medium BM2 set forth in EXAMPLE 1 herein. Conifer embryogenic cells are typically transferred to fresh maintenance medium once per week.

Development

In accordance with the methods of this aspect of the invention, a culture comprising immature conifer somatic embryos is incubated in a development medium that promotes the development of cotyledonary embryos for a first incubation period.

The development medium for use in this aspect of the invention typically contains nutrients that, sustain the somatic embryos. Suitable development media typically do not include growth-promoting hormones, such as auxins and cytokinins. The osmolality of the development medium is in the range of from 300 mM/Kg to 450 mM/Kg. In some embodiments, the development medium has an osmolality of 350 mM or higher. The development medium may be liquid, solid, or semi-solid. An example of a suitable development medium $BM_3$ is set forth in EXAMPLE 1 herein. Other examples of a suitable development media are set forth in EXAMPLES 2-4 herein. In some embodiments of the method, the development medium has an initial osmolality of at least 300 mM/kg which is maintained at a level of at least 200 mM/kg during stratification.

In some embodiments, the development medium comprises PEG at a concentration from 1% to 15%. In some embodiments, the development medium comprises PEG at a concentration of 7% to 15% (e.g., 7%, 8%, 9%, 10%, 11%, 12%, 13%, 14%, 15%). In some embodiments, the development medium comprises PEG at a concentration from 10% to 12% and an osmolality of at least 350 mM/kg to 450mM/kg.

Maltose may be included in the development medium as the principal or sole source of sugar for the somatic embryos. Useful maltose concentrations are within the range of from about 1% to about 2.5%.

The development medium may contain gellan gum. Gellan gum is a gelling agent marketed, for example, under the names GELRITE and PHYTAGEL. If gellan gum is included in the development medium, it is typically present at a concentration less than about 0.5%, typically at a concentration from about 0% to about 0.4%. The development medium is typically a solid medium, although it can be a liquid medium.

The development medium may contain an absorbent composition, such as activated charcoal, as described herein, for the induction medium.

In some embodiments, the development medium further comprises sucrose and/or abscisic acid. The concentration of abscisic acid in the development medium may be between 0.5 mg/L and 500 mg/L. In some embodiments of the methods of the invention, the concentration of abscisic acid in the development medium is between 1 mg/L and 100 mg/L. In some embodiments, the concentration of abscisic acid in the development medium is between 5 mg/L and 20 mg/L.

In some embodiments of the invention, the development medium contains sucrose as the principal or sole source of metabolizable sugar. Useful sucrose concentrations are within the range of about 1% to about 6%.

In accordance with the methods of this aspect of the invention, the culture comprising immature conifer somatic embryos is incubated in a culture vessel comprising the development medium having an osmolality in the range of from 300 mM/Kg to 450 mM/Kg at a temperature of from 22° C. to 25° C. for a first incubation period sufficient in length for at least a portion of the embryos to reach anatomical maturity (i.e., possessing developed cotyledons and hypocotyl). In some embodiments, the first incubation period is sufficient in length for at least a portion (e.g., at least one embryo, at least 10% of the embryos, at least 25%, at least 50%, more than 50%, or at least 75%) of the plurality of embryos in the embryo culture lo reach anatomical maturity.

Figure 1:
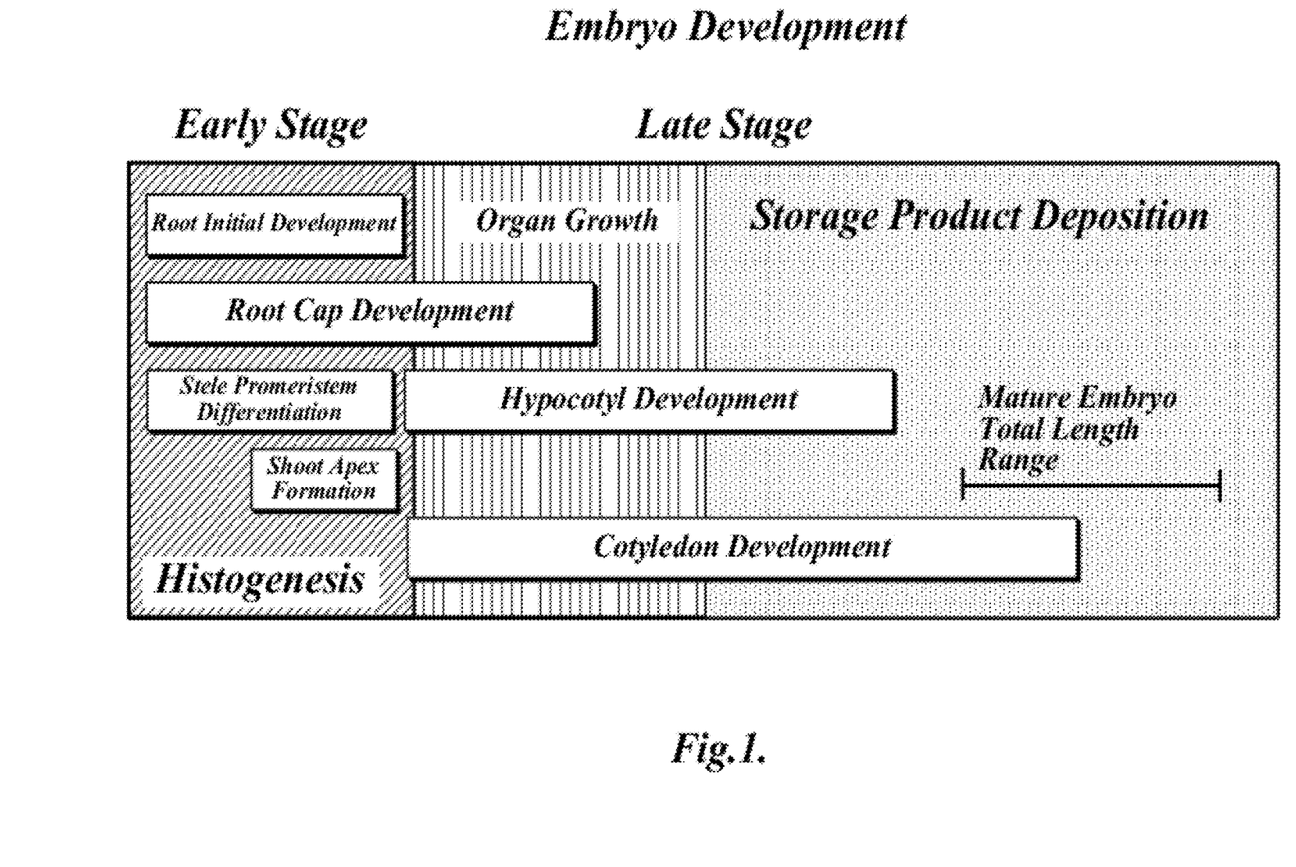
FIG. 1 is a diagrammatic representation of early and late stage development of conifer somatic embryos.

As shown in FIG. 1, the development stage of somatic embryos may be divided into the early stage which involves histogenesis (i.e., the formation of different tissues from undifferentiated cells), mid-stage which involves organ growth and the initiation of hypocotyl development and cotyledon development, and the late stage which involves the completion of organ growth, the completion of hypocotyl and cotyledon development (i.e., anatomical maturity) and storage product deposition. In particular, early stage development of an immature embryo includes root initial development, the beginning of root cap development, stele promeristem differentiation, and shoot apex formation. Mid-stage development includes the initiation of hypocotyl development and cotyledon development, and late stage development includes completion of hypocotyl development and cotyledon development, resulting in an anatomically mature embryo.

The formation of one or more structures on one or more embryos (e.g., cotyledonary primordia, or cotyledons) may be determined by visual inspection or imaging analysis of the cultured embryos. Visual inspection or imaging analysis may be optionally earned out under 5-10× magnification.

The first incubation period may be different depending on the genotype. In some embodiments, the first incubation period is from at least 6 weeks to at least 12 weeks in length, such as from eight to twelve weeks. The first incubation on the development media may be carried out at a temperature from 10° C. to 30° C., such as from 15° C. to 25° C., or such as from 20° C. to 23° C.

Stratification

Stratification (moist chilling) is a treatment used for overcoming germination resistance in the seeds of many temperate species (Taylor & Waring, *Plant, Cell, And Environment* 2:165-171, 1979). As described herein, it has been unexpectedly found that stratification may be carried out on development media comprising an osmolality of at least 300 mM/Kg up to 450 mM/kg, resulting in an increased yield of embryos, having an increased germination frequency (as described in EXAMPLES 2-4) in comparison to embryos produced using the stratification medium having an osmolality of less than 150 mM/kg (such as $BM_4$).

In accordance with the methods of this aspect of the invention, after incubating the somatic embryos on the development media for the first incubation period sufficient in length for at least a portion of the embryos to reach anatomical maturity, the embryos are then subjected to a temperature of from 0° C. to 10° C. for a second incubation period of at least 1 week to produce stratified cotyledonary somatic embryos.

In one embodiment, cotyledonary pine somatic embryos in or on the development medium comprising an osmolality of at least 300 mM/Kg up to 450 mM/kg, are subjected to a temperature of from 0° C. to 10° C. for a second incubation period of at least 1 week up to 8 weeks (e.g., from 1 week to 8 weeks, such as from 4 weeks to 6 weeks), to produce stratified cotyledonary somatic embryos. In another embodiment, cotyledonary pine somatic embryos in or on the development medium comprising an osmolality of at least 300 mM/Kg up to 450 mM/kg, are subjected to a temperature of from 0° C. to 10° C. for a second incubation period of at least 2 months up to 6 months (e.g., at least 2 months, at least 3 months, at least 4 months, at least 5 months up to 6 months), to produce stratified cotyledonary somatic embryos that are stored prior to germination. The second incubation period is typically carried out in the dark at a temperature of from 1° C. to 6° C., such as from 1° C. to 4° C.

In one embodiment of the method of the invention, the initial osmolality of the development media at the start of the first incubation period in accordance with step (a) is at least 300 mM/Kg, and is maintained at a level of at least 200 mM/kg during the second incubation period in accordance with step (b). The osmolality level may be maintained by the addition of various osmoticants to the development media (e.g., PEG, the addition of various sugars, myo-inositol, or other osmoticants to increase osmolality) or by adjusting the volume of the development media the embryos are incubated in or on during development, and stratification, as described in EXAMPLE 4.

Typically, embryos form on the surface of a mass of embryogenic cells, such as an embryonal suspensor mass. The cotyledonary embryos may be separated into individual (singulated) cotyledonary embryos before culturing them in, or on, the stratification medium, or they may be cultured as a mass of un-singulated embryos. The cotyledonary embryos may be separated into individual (singulated) cotyledonary embryos before subjecting them to a temperature of from 0° C. to 10° C. for a second incubation period of at least 1 week to produce stratified cotyledonary somatic embryos, or they may be cultured as a mass of un-singulated embryos.

Post—Stratification

After stratification, the cotyledonary embryos produced using the methods of the invention can optionally be germinated to form pine plants which can be grown into pine trees, if desired. Typically, cotyledonary embryos are subjected to a drying treatment before germination, as described in EXAMPLE 1. The cotyledonary embryos may also be disposed within manufactured seeds for subsequent germination. The cotyledonary embryos can be germinated, for example, on a solid germination medium, such as $BM_5$ medium set forth in EXAMPLE 1 herein. Typically, the cotyledonary somatic embryos are illuminated to stimulate germination. Typically, all the steps of the methods of the invention, except germination, are conducted in the dark. The germinated plants may be transferred to soil for further growth. For example, the germinated plants may be planted in soil in a greenhouse and allowed to grow before being transplanted to an outdoor site.

In some embodiments, the methods of this aspect of the invention produce a higher yield of somatic cotyledonary embryos than an identical method in which the embryogenic cells are cultured on a development medium having an osmolality of at least 300 mM/Kg up to 450 mM/kg (e.g., that contains PEG), followed by stratification in or on a stratification medium having an osmolality of less than 150 mM/kg (e.g., that does not contain PEG), as shown in EXAMPLES 2-4.

In another aspect, a method is provided for producing cotyledonary somatic embryos. The method comprises (a) incubating a culture comprising pre-cotyledonary conifer somatic embryos in or on a first development medium for a first incubation period; (b) singulating a plurality of the embryos treated in accordance with step (a); (c) culturing the plurality of singulated cotyledonary conifer somatic embryos in a culture vessel comprising a development medium having an osmolality in the range of from 300 mM/Kg to 450 mM/Kg at a temperature of from 22° C. to 25° C. for a second incubation period sufficient in length for at least a portion of the embryos to reach anatomical maturity; and (d) subjecting the embryos in the culture vessel in accordance with step (c) to a temperature of from 0° C. to 10° C. for a third incubation period of at least 1 week to produce stratified cotyledonary somatic embryos.

In accordance with this aspect of the invention, immature conifer somatic embryos, such as, for example, pre-cotyledonary conifer somatic embryos, can be prepared from conifer somatic cells, such as cells obtained from conifer embryos, by culturing the cells in, or on, an induction medium to produce embryogenic cells, as described above. The embryogenic cells may then be cultured in, or on, a maintenance medium to multiply the embryogenic cells, as described above. The multiplied embryogenic cells may then be cultured in, or on, a first development medium for a first incubation period, singulated, and incubated in a second development medium for a second incubation period, followed by stratification on the second development medium.

The first and second development media typically contain nutrients that sustain the somatic embryos. Suitable development media typically do not include growth-promoting hormones, such as auxins and cytokinins. In some embodiments, the first and second development media have the same formulation. In some embodiments, the first and second development media have different formulations.

The osmolality of the first and/or second development medium can be adjusted to a value that falls within a desired range, such as from about 300 mM/Kg to about 450 mM/Kg. Typically, an osmolality of 350 mM or higher is advantageous in the methods of the invention. An example, of a suitable development medium $BM_3$ is set forth in EXAMPLE 1 herein. Other examples of suitable development media are set forth in EXAMPLES 2-4 herein, in some embodiments of the method, the second development medium has a higher osmolality (e.g., from 350 mM/Kg to 450 mM/Kg) than the first development medium (e.g., from 300 mM/Kg to 400 mM/Kg). In some embodiments, the osmolality of the second development media is chosen to match the osmolality of the first development media at the end of the first incubation period.

In some embodiments, the first and/or second development medium comprises PEG at a concentration of from 1% to 15%. In some embodiments, the first development medium comprises PEG at a concentration of 7% to 10% (e.g., 7%, 8%. 9%, 10%). In some embodiments, the second development medium comprises PEG at a concentration of 8% to 15% (e.g., 8%, 9%, 10%, 11%, 12%, 13%, 14%, 15%). In some embodiments, the second development medium comprises PEG at a higher concentration than the fust development medium.

Maltose may be included in the first and/or second development medium as the principal or sole source of sugar for the somatic embryos. Useful maltose concentrations are within the range of from about 1% to about 2.5%.

The first and/or second development medium may contain gellan gum. Gellan gum is a gelling agent marketed, for example, under the names GELRITE and PHYTAGEL. If gellan gum is included in the development medium, it is typically present at a concentration less than about 0.5%, typically at a concentration from about 0% to about 0.4%. The first and second development media are typically a solid medium, although one or both can be a liquid medium.

The first and/or second development medium may contain an absorbent composition, such as activated charcoal, as described herein, for the induction medium.

In some embodiments, the first and/or second development medium further comprises sucrose and/or abscisic acid. The concentration of abscisic acid in the development medium may be between 0-5 mg/L and 500 mg/L. In some embodiments of the methods of the invention, the concentration of abscisic acid in the development medium is between 1 mg/L and 100 mg/L. In some embodiments, the concentration of abscisic acid in the development medium is between 5 mg/L and 20 mg/L.

In some embodiments of the invention, the first and/or second development medium contains sucrose as the principal or sole source of metabolizable sugar. Useful sucrose concentrations are within the range of about 1% to about 6%.

The first and second development medium may be liquid, solid or semi-solid. The concentrations of osmoticants, such as polyethylene glycol (PEG), or other osmoticants, may be elevated in a liquid medium to produce the same osmolality as that of the corresponding solid medium. Typically, a solid development medium that is equivalent to a liquid development medium has an osmolality that is within about 50 mM/kg of the osmolality of the liquid development medium.

In some embodiments of this aspect of the method, the first incubation period is sufficient in length for the formation of at least one of the following structures on a portion (e.g., at least one embryo, at least 10% of the embryos, at least 25%, at least 50%, more than 50%, or at least 75%) of the plurality of embryos in the first embryo culture: one or more embryos with cotyledonary primordia; one or more embryos with cotyledons; one or more embryos with 4+ cotyledons; or one or more embryos with distinct, cotyledons with hypocotyl and root regions present.

The first incubation period may be different depending on the genotype. In some embodiments, the first incubation period is from at least 6 weeks to at least 8 weeks in length, such as from 7 to 8 weeks. The first incubation on the first development media may be carried out at a temperature from 10° C. to 30° C., such as from 15° C. to 25° C., or such as from 20° C. to 23° C.

At the end of the first incubation period, for example, when the presence of one or more cotyledonary primordia is observed on a portion of embryos, or after a time period of at least 6 weeks, the method comprises singulating a plurality of individual embryos from the first culture of embryos.

Any means of physically separating individual embryos from the first culture of embryos may be used to singulate the embryos in accordance with the methods of the invention. For example, in the context of an embryonal suspensor mass (ESM) culture, physical methods of separation may be used, such as washing away the ESM (e.g., spray singulation via pressure-controlled spray of aqueous liquid), vacuuming away the ESM, vibration, or picking the embryos from the ESM. Other non-limiting examples of useful singulation methods include filtering or sorting embryos based on a physical attribute such as size, shape, for example through a sieve, or based on other physical attributes such as surface roughness, hydrophobicity, density or mass.

In some embodiments, the singulation step further comprises picking individual embryos based on one or more selection criteria. For example, visually evaluated screening criteria may be used by a skilled technician or a computerized imaging system to select embryos based on one or more morphological features including, but not limited to, the embryo's size, shape (e.g., axial symmetry), surface texture, color (e.g., no visible greening), absence of split hypocotyls, and no translucent cotyledons. Embryos can also be selected based on criteria relating to chemistry or external structure adsorption, reflectance, transmittance, or emission spectra through the use of near infrared spectroscopy (NIR), as described in U.S. Patent Application No. 2004/0072143 entitled "Methods for Classification of Somatic Embryos," incorporated herein by reference.

Desirable embryos may be individually picked (via a manual or automated process) out of the first embryo culture (e.g., such as an embryonal suspensor mass), with any suitable instrument, such as tweezers. The embryo picking may be carried out manually or via an automated process, such as described in U.S. Patent Application No. 2004/0267457, entitled "Automated System and Method for Harvesting and Multi-Stage Screening of Plant Embryos," incorporated herein by reference.

In some embodiments of the method, the picked embryos are laid out directly onto the surface of a second development medium, or onto a porous substrate in contact with a second development medium, which may be in solid or liquid form.

A porous substrate that is useful in the practice of various embodiments of the methods of the invention typically has a pore diameter in the range of from about 5 microns to about 1200 microns, such as from about 50 to 500 microns, such as from about 70 to about 150 microns, such as about 100 microns. The porous material is typically planar and may be any desired shape or dimension chosen for ease of manipulation and for placement in contact with the second development media. Exemplary porous materials include materials that are sterilizable and sufficiently strong to resist tearing when the materials are lifted in order to transfer singulated embryos to subsequent stages of the somatic embryo production process, such as stratification. Examples of useful porous materials include, but are not limited to, membranes, nylon fiber, woven mesh (e.g., nylon, stainless steel or plastic), and polymeric fibers.

In some embodiments, the singulated embryos are transferred to a second development media, or a porous substrate in contact with a second development media, in such a manner that the singulated embryos are not in physical contact with one another.

According to the methods of the invention, after singulation, the singulated immature embryos are contacted with a second development medium for a second incubation period. In some embodiments, the second incubation period is sufficient in length for at least a portion (e.g., at least one embryo, at least 10% of the embryos, at least 25%, at least 50%, more than 50%, or at least 75%) of the plurality of singulated embryos to reach anatomical maturity (i.e., possessing developed cotyledons and hypocotyl), as described above with reference to FIG. 1.

The second incubation period may be different depending on the genotype. In some embodiments, the second incubation period is at least 3 weeks in length, such as 3 weeks to 5 weeks. In some embodiments, the embryos are incubated for a total length of time (including the first incubation period and the second incubation period) of at least 12 weeks on development media. The second incubation on the second development media may be carried out at a temperature from 10° C. to 30° C., such as from 15° C. to 25° C., or such as from 20° C. to 23° C.

In accordance with this aspect of the methods of the invention, after incubation in or on the second development medium, the singulated embryos are then stratified by subjecting them to a temperature of from 0° C. to 10° C. for a third incubation period of at least 1 week.

In one embodiment, cotyledonary pine somatic embryos in or on the development medium comprising an osmolality of at least 300 mM/Kg up to 450 mM/kg, are subjected to a temperature of from 0° C. to 10° C. for a third incubation period of at least 1 week up to 8 weeks (e.g., from 1 week to 8 weeks, such as from 4 weeks to 6 weeks), to produce stratified cotyledonary somatic embryos. In another embodiment, cotyledonary pine somatic embryos in or on the development medium comprising an osmolality of at least 300 mM/Kg up to 450 mM/kg, are subjected to a temperature of from 0° C. to 10° C. for a third incubation period of at least 2 months up to 6 months (e.g., at least 2 months, at least 3 months, at least 4 months, at least 5 months up to 6 months), to produce stratified cotyledonary somatic embryos that are stored prior to germination. The third incubation period is typically carried out in the dark at a temperature of from 1° C. to 6° C., such as from 1° C. to 4° C.

In one embodiment of the method of the invention, the initial osmolality of the development media at the start of the second incubation period in accordance with step (a) is at least 300 mM/Kg, and is maintained at a level of at least 200 mM/kg during the third incubation period in accordance with step (c).

The methods of the various aspects of the invention each include the step of incubating a culture comprising immature conifer somatic embryos in a development medium having an osmolality in the range of from 300 mM/kg to 450 mM/kg for a first incubation period followed by subjecting the embryos in the culture vessel to a temperature of from 0° C. to 10° C. for at least 1 week to produce stratified embryos. The methods of the invention can be used, for example, to produce clones of individual pine trees that possess one or more desirable characteristics, such as a rapid growth rate. Thus, in one aspect, the present, invention provides methods for producing a population of genetically-identical pine somatic embryos.

The term "genetically-identical pine somatic embryos" as used herein refers to embryos that are derived from the same original plant. The term includes pine somatic embryos containing a small number of mutations that may occur during the development of somatic embryos. Any of the methods described herein can be used to produce populations of genetically-identical cotyledonary somatic pine embryos.

The following examples merely illustrate the best mode now contemplated for practicing the invention, but should not be construed to limit the invention.

EXAMPLE 1

This Example describes a method for producing somatic pine embryos from *Loblolly* Pine using development medium ($BM_3$) and stratification medium ($BM_4$).

Methods:

Female gametophytes containing zygotic embryos are removed from seeds 4 weeks to 5 weeks after fertilization. The seed coats are removed but the embryos are not further dissected out of the surrounding gamelophyte other than to excise the nucellar end. The cones are stored at 4° C. until used. Immediately before removal of the immature embryos the seeds are sterilized utilizing an initial washing and detergent treatment followed by a ten minute sterilization in 15% $H_2O_2$. The explants are thoroughly washed with sterile distilled water after each treatment.

Tables 3 and 2 set forth the compositions of media useful for producing pine somatic embryos.

TABLE 1

*Pinus Taeda* Basal Medium (BM)

| Constituent | Concentration (mg/L) |
|---|---|
| $NH_4NO_3$ | 150.0 |
| $KNO_3$ | 909.9 |
| $KH_2PO_4$ | 136.1 |
| $Ca(NO_3)_2 \cdot 4H_2O$ | 236.2 |
| $CaCl_2 \cdot 4H_2O$ | 50.0 |
| $MgSO_4 \cdot 7H_2O$ | 246.5 |
| $Mg(NO_3)_2 \cdot 6H_2O$ | 256.5 |
| $MgCl_2 \cdot 6H_2O$ | 50.0 |
| KI | 4.15 |
| $H_3BO_3$ | 15.5 |
| $MnSO_4 \cdot H_2O$ | 10.5 |
| $ZnSO_4 \cdot 7H_2O$ | 14.4 |
| $NaMoO_4 \cdot 2H_2O$ | 0.125 |
| $CuSO_4 \cdot 5H_2O$ | 0.125 |
| $CoCl_2 \cdot 6H_2O$ | 0.125 |
| $FeSO_4 \cdot 7H_2O$ | 27.86 |
| $Na_2EDTA$ | 37.36 |
| Maltose | 30,000 |
| myo-Inositol | 200 |
| Casamino acids | 500 |
| L-Glutamine | 1000 |
| Thiamine•HCl | 1.00 |
| Pyridoxine•HCl | 0.50 |
| Nicotinic acid | 0.50 |
| Glycine | 2.00 |
| Gelrite | 1600 | pH adjusted to 5.7
†Used if a solid medium is desired

TABLE 2

Composition of Media for Different Stage Treatments

| | |
|---|---|
| $BM_1$-Induction Medium | BM + 2,4-D (15 µM) + Kinetin (2 µM) + BAP (2 µM). |
| $BM_2$-Maintenance | BM + 2,4-D (5 µM) + Kinetin (0.5 µM) + BAP (0.5 µM), Gelrite |

TABLE 2-continued

Composition of Media for Different Stage Treatments

| Medium | |
|---|---|
| | (1600 mg/L) is added when a solid medium is desired. |
| $BM_3$-Development Medium | BM + 25 mg/L abscisic acid + 10% PEG-8000 + 0.01% myo-inositol, +0.1% activated charcoal + 1% glucose, +2.5% maltose. The following amino acid mixture is added: L-proline (100 mg/L), L-asparagine (100 mg/L), L-arginine (50 mg/L), L-alanine (20 mg/L), and L-serine (20 mg/L). Gelrite (2500 mg/L) is added when a solid medium is desired. Osmolality = 365 mM/kg |
| $BM_4$-Stratification Medium | $BM_3$ modified by omitting abscisic acid and omitting PEG-8000. Gelrite (2500 mg/L) is added when a solid medium is desired. Osmolality = 120 mM/kg |
| $BM_5$-Germination Medium | BM modified by replacing maltose with 2% sucrose. Myo-inositol is reduced to 100 mg/L, glutamine and casamino acids are reduced to 0.0 mg/L, $FeSO_4 \cdot 7H_2O$ is reduced to 13.9 mg/L, and $Na_2EDTA$ is reduced to 18.6 mg/L. Gelrite replaced with 8 g/L agar, and 0.25% activated charcoal is added. |

Induction: Sterile gametophytes with intact embryos are placed on a solid $BM_1$ culture medium and held in an environment at 22°-25 C with a 24 hour dark photoperiod for a time of 3 weeks to 5 weeks. The length of time depends on the particular genotype being cultured. At the end of this time a white mucilaginous mass forms in association with the original explants. Microscopic examination typically reveals numerous early stage embryos associated with the mass. These are generally characterized as having a long thin-walled suspensor associated with a small head with dense cytoplasm and large nuclei.

Osmolality of the induction medium may in some instances be as high as 150 mM/kg, and is typically about 120 mM/kg or even lower (such as 110 mM/kg).

Maintenance and Multiplication: Early stage embryos removed from the masses generated in the induction stage are first placed on a $BM_2$ gelled maintenance and multiplication medium. This differs from the induction medium in that, the growth hormones (both auxins and cytokinins) are reduced by at least a full order of magnitude. Osmolality of this medium is at 120 mM/kg or higher (typically within the range of about 120-150 mM/kg for *Pinus taeda*). The temperature and photoperiod were again 22°-25° C. with 24 hours in (be dark. Embryos are cultured 12-14 days on the $BM_2$ solid medium before transferring to a liquid medium for further subculturing. This liquid medium has the same composition as $BM_2$, but lacks the gellant. The embryos at the end of the solid maintenance stage are typically similar in appearance to those from the induction stage. After 5 to 6 weekly subcultures on the liquid maintenance medium, advanced early stage embryos have formed. These are characterized by smooth embryonal heads, estimated to typically have over 100 individual cells, with multiple suspensors.

Embryo Development: Early stage immature embryos are transferred from maintenance medium to a solid development medium. The development medium either lacks growth hormones entirely, or has them present only at very low levels. Abscisic acid is typically included to facilitate further development. The further inclusion of an adsorbent composition in this medium is advantageous. The absorbent composition may be chosen from a number of chemical materials having high surface area and/or controlled pore size, such as activated charcoal, soluble and insoluble forms of poly(vinyl pyrrolidone), activated alumina, and silica gel. The adsorbent, composition is normally present at a concentration of about 0.1-5 g/L, more generally about 0.25-2.5 g/L. Gellan gum may be included at a concentration of about 0.25%.

The osmotic potential of the development medium may be raised substantially over that of the maintenance medium. It has been found advantageous to have an osmolality as high as 360 mM/kg or higher, (e.g. up to 450 mM/kg). Development is preferably carried out in complete darkness at a temperature of 22° C.-25° C. until cotyledonary embryos have developed (e.g., reached anatomical maturity).

Maturation and Stratification:

After 7 to 12 weeks on development medium $BM_3$, cotyledonary embryos are singulated and transferred to a filter paper support on stratification medium $BM_4$. The stratification medium $BM_4$ is similar to development medium $BM_3$ but lacks abscisic acid, PEG-8000 and gellan gum. The osmolality of stratification medium without PEG is typically below 150 mM/kg, such as about 120 mM/kg. Embryos are cultivated on stratification medium at between 1° C. and about 10° C. in the dark for between 1 week to 8 weeks, such as for between 2 weeks to 6 weeks.

Drying: The mature embryos still on their filter paper support are lifted from the pad and placed in a closed container over water, at a relative humidity of 97% to 99%, for a period of about 3 weeks.

Germination: The dried mature embryos are rehydrated by placing them, while still on the filter paper support, for about 24 hours on a pad saturated with liquid germination medium. The embryos are then placed individually on solid $BM_5$ medium for germination. This is a basal medium lacking growth hormones which has been modified by reducing sucrose, myo-inositol and organic nitrogen. The embryos are incubated on $BM_5$ medium for about 10 weeks under environmental conditions of 23°-25° C., and a 16 hour light-8 hour dark photoperiod, until the resulting plantlets have a well developed radicle and hypocotyl and green cotyledonary structure and epicotyl.

Because of the reduced carbohydrate concentration, the osmotic potential of the germination medium is further reduced below that of the development medium. It is normally below about 150 mM/kg (such as about 100 mM/kg).

EXAMPLE 2

This Example demonstrates that incubation of immature Loblolly pine (*Pinus taeda*) embryos on development medium (+10% PEG) having an osmolality of 365 mM/kg followed by stratification while on the same development medium, improves embryo yield and successful germination as compared to incubation of embryos on development medium having an osmolality of 365 mM/kg followed by stratification on a stratification medium (0.0% PEG) having an osmolality less than 150 mM/kg.

Methods:

Female gametophytes containing zygotic embryos were removed from seeds of seven different genotypes according to the methods described in EXAMPLE 1. The induction and maintenances stages were as described in EXAMPLE 1, and stocks of embryonal suspensor mass (ESM) cultures were frozen.

Recovery of ESM Cultures from Cryostorage:

One vial of each genotype was thawed on filter paper over maintenance medium $BM_2$. Once the cultures had grown enough ESM to form a mound of about 1 cm in width and 0.4 cm in height, the ESM was collected off the filter paper and cleaned of callus. This transfer process continued on for a 14-day cycle, until 1-4 mounds of ESM about 1 cm in width and 0.4 cm in height were collected for each genotype.

Maintenance and Multiplication

Approximately 7 weeks after recovery of ESM from frozen stocks, the ESM cultures were bulked up to a 500 ml flask containing 100 ml of maintenance media at a ratio of 1:5.

Development:

The ESM culture was plated onto a nylon membrane over 600 ml of semi-solid development media $BM_3$ (+10% PEG, osmolality=365 mM/kg) in half-size (shallow) Cambro boxes (2" depth), resulting in a media depth of approximately ½ inch. A total of 24 ml of cells was plated for each genotype onto two half-size Cambro boxes. Each frame in a Cambro box had 6 ml of cells for a total of 12 ml of cells per box in a twelve drop configuration. The cells were dispensed in 12 drops of 0.5 ml each per frame. After plating, the Cambro boxes were placed in the dark at room temperature for a development period of 12 weeks. Following the development period, the following stratification treatments were tested, as described below in TABLE 3.

Stratification:

After 12 weeks incubation on development media $BM_3$, the embryos in Treatment Groups 1 and 8 were transferred onto a pad over 320 ml stratification medium $BM_4$ (0.0% PEG, osmolality=120 mM/kg) contained in half size Cambro boxes. The embryos in Treatment Group 14 were maintained on development media $BM_3$ during stratification. Stratification of all treatment groups was carried out for 4 weeks at 4° C. to 7° C.

TABLE 3

DESCRIPTION OF POST-DEVELOPMENT TREATMENT CONDITIONS

| Treatment Reference Number | Description of Treatment | # of clones tested |
|---|---|---|
| 1 (control) | 12 week incubation in development media $BM_3$ at room temperature, stratification in stratification media $BM_4$ for 1 month, COW for 1 week, germination for 5 weeks. | 61 |
| 8 | 12 week incubation in development media $BM_3$ at room temperature, 3 month storage in the dark at 4-8° C., stratification in stratification media $BM_4$ for 1 month, COW for 1 week, germination for 5 weeks. | 30 |
| 14 | 12 week incubation in development media $BM_3$ at room temperature, after development Cambro boxes were stored in the dark at 4° C. to 8° C. for 3 | 15 |

TABLE 3-continued

DESCRIPTION OF POST-DEVELOPMENT TREATMENT CONDITIONS

| Treatment Reference Number | Description of Treatment | # of clones tested |
|---|---|---|
| | months in development media $BM_3$. (no media change), COW for 1 week, germination for 5 weeks. | |

Conditioning Over Water (COW) and Singulation:

Following stratification, embryos were singulated by spray separation and then placed in a 98% relative humidity environment and conditioned over water at room temperature for 1 week in COW boxes.

Germination:

Following conditioning over water, 75 embryos of each treatment (per genotype) were transferred by hand to germination media $BM_5$ (150 ml media dispensed per Cambro box). These embryos were laid on top of the germination media and not planted. 25 embryos were placed in each box, resulting in 3 germination boxes per treatment per genotype. Any remaining embryos were counted to determine total embryo yield.

Embryos were visually selected for germination using the following criteria: three or more visible cotyledons; smooth embryo (no callusing); embryo color is ivory, yellow or green in color and opaque; embryos fused together were not selected; embryos with wide flattened hypocotyls were not selected; and elongated embryos were accepted.

Following manual embryo transfer to germination boxes containing germination media, the boxes were placed at 1° C. to 2° C. for 3 months. The germination boxes were then moved to room temperature in the dark for 7 days, then placed in a light room to continue germination. After 8 weeks of incubation on germination media, the germinants were monitored to determine whether they were ready for transplant to the greenhouse. Germinants for treatment 1 (control) were harvested when the majority met the selection criteria. All subsequent experimental treatments were harvested using the control germination period for each individual genotype clone.

Results:

Comparison between Treatment 1 (Control) and Treatment 14

This experiment compares continued incubation of embryos on development media during stratification (omitting use of stratification media) (treatment 14), with the control treatment 1, in which embryos were incubated on development media, and transferred to stratification media prior to stratification. As shown below in TABLE 4, treatment 14 produced embryos with a higher germination frequency, and germinants with improved vigor as compared to embryos produced from treatment 1.

TABLE 4

ESTIMATED MEAN GERMINATION FREQUENCY AND CONFIDENCE INTERVALS FOR TREATMENT 1 AND 14 (N = 15 GENOTYPES)

| Treatment | Estimated Mean Germination Frequency | Lower 90% Confidence Interval (CI) | Upper 90% Confidence Interval (CI) |
|---|---|---|---|
| 1 (control) | 0.335 | 0.280 | 0.395 |
| 14 (strat on dev | 0.373 | 0.316 | 0.434 |

TABLE 4-continued

ESTIMATED MEAN GERMINATION FREQUENCY
AND CONFIDENCE INTERVALS FOR TREATMENT
1 AND 14 (N = 15 GENOTYPES)

| Treatment | Estimated Mean Germination Frequency | Lower 90% Confidence Interval (CI) | Upper 90% Confidence Interval (CI) |
|---|---|---|---|
| media in cold storage) | | | |

As shown above in TABLE 4, embryos from treatment group 14 had slightly greater germination frequencies (37%) than the control treatment 1 (34%), although the difference observed was not statistically significant (p=0.42).

TABLE 5

ESTIMATED MEAN SURVIVAL AND CONFIDENCE
INTERVALS FOR TREATMENTS 1 AND 14
(N = 15 GENOTYPES)

| Treatment | Estimated Mean Survival | Lower 90% Confidence Interval | Upper 90% Confidence Interval |
|---|---|---|---|
| 1 | 0.756 | 0.690 | 0.812 |
| 14 | 0.748 | 0.686 | 0.802 |

As shown above in TABLE 5, germinants generated using Treatment 14 had a slightly lower survival than Treatment 1 (control) (75% versus 76%), but the difference was not statistically significant (p=0.87).

Figure 2A:
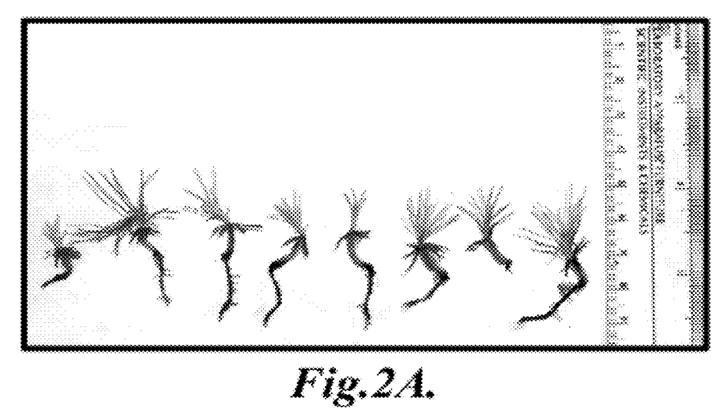
FIG. 2A is a photograph of germinants from treatment group 1, S-frame 1.
Figure 2B:
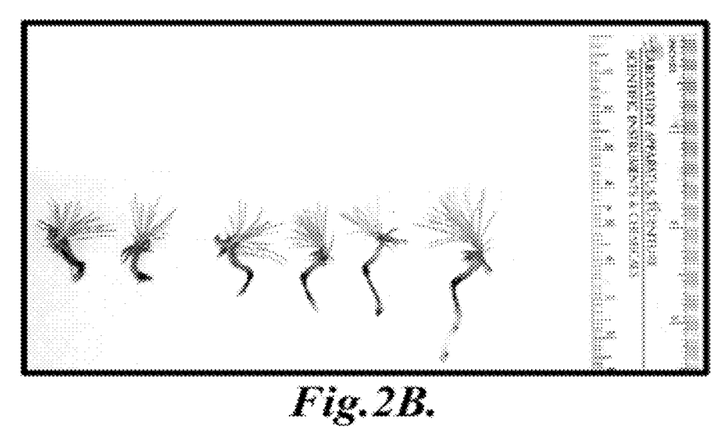
FIG. 2B is a photograph of germinants from treatment group 1, S-frame 2.
Figure 2C:
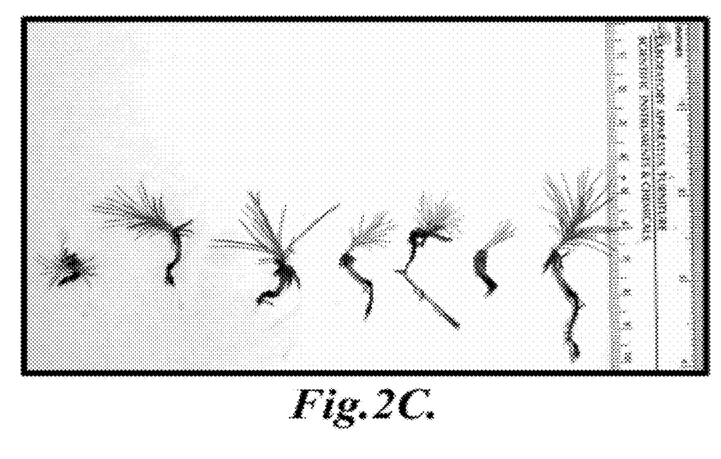
FIG. 2C is a photograph of germinants from treatment group 1, S-frame 3.
Figure 2D:
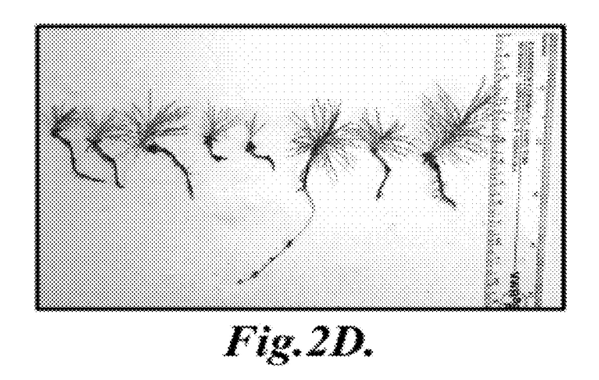
FIG. 2D is a photograph of germinants from treatment group 14, S-frame 1.
Figure 2E:
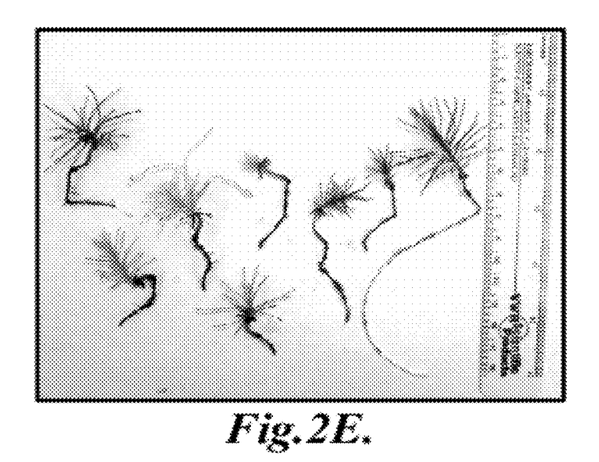
FIG. 2E is a photograph of germinants from treatment group 14, S-frame 2.
Figure 2F:
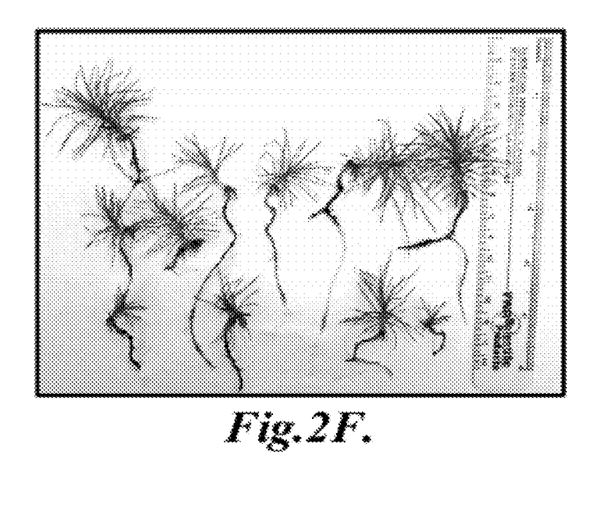
FIG. 2F is a photograph of germinants from treatment group 14, S-frame 3.

An improvement in germinant vigor was observed in favor of treatment 14. Thirteen of the 15 genotypes included in treatment group 14 were observed to have more vigorous epicotyl, longer roots, or both, than embryos from treatment group 1. Although organ lengths were not measured in this experiment, pictures were taken of the germinants in each treatment group prior to transplant. FIG. 2 is a panel of photographs of germinants produced under treatment group 1 (control) conditions (FIGS. 2A-2C), or produced under treatment group 14 conditions (FIGS. 2D-2F). As shown in FIG. 2, an improvement in germinant vigor was obtained using the conditions of treatment group 14 (FIGS. 2D-F) as compared to treatment group 1 (control) (FIGS. 2A-C).

Comparison of Treatments 1, 8, and 14

This analysis compares the results for genotypes that were shared in treatments 1,8, and 14 in order to determine if transferring embryos to stratification media following incubation and optional storage in development media was detrimental to the germination of the embryos. The germination frequency results are shown in TABLE 6.

TABLE 6

MEAN GERMINATION FREQUENCY AND CONFIDENCE
INTERVALS FOR TREATMENTS 1, 8 AND 14
(N = 7 GENOTYPES)

| Treatment | Estimated Mean Germination Frequency | Lower 90% Confidence Interval | Upper 90% Confidence Interval |
|---|---|---|---|
| 1 (control) | 0.396 | 0.315 | 0.484 |
| 8 | 0.180 | 0.125 | 0.254 |
| 14 | 0.403 | 0.321 | 0.491 |

The difference in germination frequencies among the control and treatments shown in TABLE 6 is statistically significant (p=0.0005). In a direct comparison between treatments 8 and 14, treatment 8 is significantly lower than treatment 14 (p=0.0008) and the control (p=0.0011). Moreover, the treatment 8 embryos were observed to be malformed following spray separation (data not shown).

Summary and Conclusion: These results demonstrate that continued incubation of embryos on development media (10% PEG, osmolality=365 mM/kg) during stratification (omitting use of stratification media) (treatment group 14) produces embryos with a higher germination frequency, and germinants with improved vigor as compared to embryos produced from treatment group 1 and treatment group 8, in which embryos were incubated on development media (10% PEG, osmolality=365 mM/kg), and transferred to stratification media (0.0% PEG, osmolality=120 mM/kg) prior to stratification. Moreover, as shown in FIG. 2, an improvement in germinant vigor was observed in favor of treatment 14, in which thirteen of the fifteen genotypes included in treatment group 14 were observed to have more vigorous epicotyl, longer roots, or both, than embryos from treatment group 1.

EXAMPLE 3

This Example demonstrates that omission of the media change step between development and stratification produces embryos with increased germination frequency.

Methods:

Female gametophytes containing zygotic embryos were removed from seeds of four different genotypes according to the methods described in EXAMPLE 1. The induction, maintenance and development, stages were carried out as described in EXAMPLE 1.

TABLE 7 describes the post-development experimental treatment conditions.

TABLE 7

POST-DEVELOPMENT TREATMENT CONDITIONS

| Treatment Reference Number | Description |
|---|---|
| 1 (control) | 12 week incubation on development media modified $BM_3$ (10% PEG, osmolality = 336 mM/kg), stratification on stratification media $BM_4$ (0% PEG, osmolality = 120 mM/kg) for 4 weeks |
| 2 | 12 week incubation on development media modified $BM_3$ (10% PEG, osmolality = 336 mM/kg), stratification on stratification media $BM_4$ (0% PEG, osmolality = 120 mM/kg) for 8 weeks |
| 3 | 12 week incubation on development media modified $BM_3$ (10% PEG, osmolality = 336 mM/kg), after development Cambro boxes were stored in the dark at 4° C. for 4 weeks on same development media (no media change) |
| 4 | same as treatment 3, with 8 week duration on development media at 4° C. |

Following the stratification treatments shown above in TABLE 7, the embryos on the d-frames were spray separated onto 3 s-frames (full cambro boxes) per genotype/treatment. Two germination boxes of 25 embryos each were selected from each s-frame. A total of 6 germination boxes were created per genotype/treatment. Embryos were placed onto the germination media, and not planted into the media. Germinants were assessed following a 6 week incubation on germination media. Root length was also measured on all the category 1 plants.

A category 1 germinant includes the following features: the presence of a 1 mm root (no nubbins), the presence of approximately 5 epicotyl leaves approximately 5 mm long, no large scale hypocotyl ruptures, and the hypocotyl not bent greater than 90 degrees.

A Category 1+2 germinant (bipolar) includes the following features: the presence of a 1 mm root (no nubbins) and the presence of epicotyl leaves (no size or number), that are visible to the eye.

Statistical Analysis:

There were 4 treatments, a full factorial comprised of 2 stratification media (standard and old development media), times two durations (4 weeks and 8 weeks). The various media was applied to the whole plot experimental units and the duration of incubation was applied to the split plots. Results were assessed by germination frequency (cat 1 and cat 1+cat 2) and root length. Root length was analyzed with a mixed model after making a natural log transformation to stabilize the variance. Category 1 and Category 1+Category 2 germinants were analyzed using a generalized linear mixed model.

The Category 1 germination frequency results are shown below in TABLE 8.

TABLE 8

CATEGORY 1 MEAN GERMINATION FREQUENCY
(ALL GENOTYPES INCLUDED)

| Treatment | Mean Germination Frequency | Lower 90% Confidence Interval (CI) | Upper 90% Confidence Interval (CI) |
|---|---|---|---|
| 1 (control) | 0.083 | 0.046 | 0.143 |
| 2 | 0.064 | 0.036 | 0.113 |
| 3 | 0.098 | 0.056 | 0.167 |
| 4 | 0.104 | 0.059 | 0.176 |

As shown above in TABLE 8, the germination frequency of Category 1 germinants was higher in treatments 3 and 4, in which embryos were maintained on development media during the stratification step (i.e., incubation at 4° C.)

The results of the total bipolar germination frequency (cat 1+cat 2) is shown below in TABLE 9.

TABLE 9

MEAN FOR TOTAL BIPOLAR GERMINATION (CAT 1 + CAT 2)
(ALL GENOTYPES INCLUDED)

| Treatment | Mean Germination Frequency | Lower 90% CI | Upper 90% CI |
|---|---|---|---|
| 1 (control) | 0.300 | 0.202 | 0.422 |
| 2 | 0.296 | 0.199 | 0.417 |
| 3 | 0.243 | 0.147 | 0.374 |
| 4 | 0.205 | 0.122 | 0.325 |

The mean value for category 1 germination frequency, or for bipolar (cat 1+cat 2) for each of the four genotypes tested only varied by about 10-20% (data not shown).

The results of the mean root length measurements are shown in TABLE 10.

TABLE 10

MEAN ROOT LENGTH (ALL GENOTYPES INCLUDED)

| Treatment | Mean (mm) | Lower 90% CI | Upper 90% CI |
|---|---|---|---|
| 1 (control) | 13.5 | 10.3 | 17.7 |
| 2 | 19.0 | 14.5 | 24.8 |
| 3 | 12.8 | 9.8 | 16.8 |
| 4 | 17.4 | 13.3 | 22.8 |

TABLE 11

COMPARISON OF TEST RESULTS FROM THE 3 MODELS

| Variable | Cat 1 Germinants P value | Bipolar Germinants (cat 1 + cat 2) P value | Root length P value |
|---|---|---|---|
| Media for stratification (stratification media v development media) | 0.07 (dev is better) | 0.42 | 0.40 |
| Duration (4 wk v 8 wk) | 0.30 | 0.09 (4 wk is better) | <0.01 (8 wk is better) |
| Media * Duration | 0.10 | 0.16 | 0.85 |

P values <0.10 indicate a significant result.

Summary of results: With regard to category 1 germination, a statistically significant difference (p=0.07) was observed in germination frequency for embryos that were maintained on development media (modified $BM_3$ 10% PEG, osmolality=336 mM/kg) during the stratification step (i.e., incubation at 4° C.), as shown in TABLE 8. With regard to duration, the embryos stratified on development media (modified $BM_3$ 10% PEG, osmolality=336 mM/kg) benefitted from an additional 4 weeks of incubation whereas those on stratification media ($BM_4$ 0.0% PEG, osmolality=120 mM/kg) did not. The overall low values of germination observed may be increased by the use of early singulation during development, followed by maintaining the embryos on the development media after singulation through the stratification period.

Overall, these results indicate that conducting the step of stratification on the original development media (i.e., omitting the step of transferring embryos to stratification media) is beneficial to obtain embryos with more vigorous category 1 germination. This is a significant result, because the omission of the transfer to stratification media allows for development, storage and stratification all on the same development media, making the process much more efficient. For example, the omission of embryo transfer from development media lo stratification reduces the labor, the preparation of stratification media, and the preparation of die additional eambro boxes.

EXAMPLE 4

This Example measures the effect of media volume, and media depth during development and stratification treatment on the germination frequency of somatic embryos.

Methods;

Female gametophytes containing zygotic embryos were removed from seeds of four different genotypes according to the methods described in EXAMPLE 1. The induction and maintenance stages were carried out as described in EXAMPLE 1, with the exception that the ESM was spread over the mesh on the development frame rather than drop-plated.

The development and stratification steps were carried out as shown below in TABLE 12. All embryos in this experiment were incubated on development medium with an initial 336 mM/kg osmolality (10% PEG) for 12 weeks, followed by stratification as shown in TABLE 12 for 4 weeks.

TABLE 12

DEVELOPMENT AND STRATIFICATION TREATMENTS

| Treatment | Media Volume | Cambro Pan-depth | Media transfer between development and stratification? | Stratification at 4° C. |
|---|---|---|---|---|
| 1 (control) | 600 ml | shallow (2") | yes | strat media (BM$_4$, 0.0% PEG, osmol = 120 mM/kg) |
| 2 | 900 ml | shallow (2") | yes | strat media (BM$_4$, 0.0% PEG, osmol = 120 mM/kg) |
| 3 | 1200 ml | shallow (2") | yes | strat media (BM$_4$, 0.0% PEG, osmol = 120 mM/kg) |
| 4 (control) | 600 ml | deep (4") | yes | strat media (BM$_4$, 0.0% PEG, osmol = 120 mM/kg) |
| 5 | 900 ml | deep (4") | yes | strat media (BM$_4$, 0.0% PEG, osmol = 120 mM/kg) |
| 6 | 1200 ml | deep (4") | yes | strat media (BM$_4$, 0.0% PEG, osmol = 120 mM/kg) |
| 7 | 600 ml | shallow (2") | no | dev media (modified BM$_3$ 10% PEG, osmol = 336 mM/kg) |
| 8 | 900 ml | shallow (2") | no | dev media (modified BM$_3$ 10% PEG, osmol = 336 mM/kg) |
| 9 | 1200 ml | shallow (2") | no | dev media (modified BM$_3$ 10% PEG, osmol = 336 mM/kg) |
| 10 | 600 ml | deep (4") | no | dev media (modified BM$_3$ 10% PEG, osmol = 336 mM/kg) |
| 11 | 900 ml | deep (4") | no | dev media (modified BM$_3$ 10% PEG, osmol = 336 mM/kg) |
| 12 | 1200 ml | deep (4") | no | dev media (modified BM$_3$ 10% PEG, osmol = 336 mM/kg) |

After development, all treatments were taken through to germination as described below.

Stratification: As shown in TABLE 12, for treatments 1-6, embryos plated onto a D-frame were moved to stratification medium (BM$_4$, 0.0% PEG, osmol=120 mM/kg). For treatments 7-12, embryos plated on a D-frame on development media (modified BM$_3$ 10% PEG, osmol=336 mM/kg) remained on the same development media during stratification.

The total yield of embryo per treatment was determined after 12 weeks incubation on development media. Conditioning over water (COW) was carried out in a large 1×1 cambro box for 1 week.

Germination: 100 embryos per treatment were manually transferred to germination boxes. Embryos selection criteria for germination: Symmetrical embryos with all three parts (cotyledon, hypocotyls and radicle regions) were chosen without obvious defects that had four or more cotyledons without any fused cotyledons or cotyledons sprouting from the center. The embryos size varied. Embryos were opaque, with color in all shades of white, yellow or green. No translucent or vitrified green embryos were selected. Germination frequency was assessed at 6 weeks.

Results:

TABLE 13 shows the effect of media volume, pan depth and media depth during development and stratification on mean embryo yield, as analyzed using a linear mixed model.

TABLE 13

STATISTICAL SIGNIFICANCE OF MEDIA VOLUME, PAN DEPTH AND MEDIA DEPTH DURING DEVELOPMENT AND STRATIFICATION

| Treatment Variable | DF (degrees of freedom) | P-Value |
|---|---|---|
| Media Volume | 2 | 0.073 |
| Pan Depth | 1 | 0.009 |
| Media Depth | 2 | 0.177 |

As shown above in TABLE 13, the effect of Cambro box-depth (pan depth) on embryo yield is statistically significant with a p-value of 0.009. The effect of media volume is weakly significant with a p-value of 0.073, while no statistical significance was observed for an interaction effect between these variables.

TABLE 14 shows the estimated mean yield ("LS Means") for each level of media volume and pan depth, along with 95% confidence intervals. As shown in the group column in TABLE 14. variables within the same group letter are not statistically significant at a 90% confidence level while factors with different group letters are significantly different.

TABLE 14

THE EFFECT OF MEDIA VOLUME AND BOX DEPTH DURING DEVELOPMENT AND STRATIFICATION ON EMBRYO YIELD

| Variable | Estimated embryo yield | Lower 90% CI | Upper 90% CI | Group |
|---|---|---|---|---|
| Media volume: 600 ml | 641 | 421 | 861 | A |
| Media volume: 900 ml | 785 | 575 | 994 | B |
| Media volume: 1200 ml | 780 | 570 | 990 | B |
| Pan depth: shallow (2") | 650 | 432 | 869 | A |
| Pan depth: deep (4") | 820 | 616 | 1024 | B |

As shown above in TABLE 14, the cambro boxes with the 900 ml and 1200 ml media volumes resulted in a statistically significant higher embryo yield than the boxes with 600 ml media volume. The 900 ml and 1200 ml volume treatments were not significantly different from each other, and each had an estimated yield that was approximately 140 embryos per box greater than the yield from the cambro box with the 600 ml volume.

TABLE 15

COMPARISON OF EMBRYO YIELD AFTER STRATIFICATION (I.E., INCUBATION AT 4° C.) ON STRATIFICATION MEDIA OR DEVELOPMENT MEDIA

| Treatment | Media Volume | Cambro Pan | Stratification | Embryo Yield |
|---|---|---|---|---|
| 1 (control) | 600 ml | shallow (2"), (media depth = ½") | strat media | 668 |
| 2 | 900 ml | shallow (2"), (media depth = ¾") | strat media | 746 |
| 3 | 1200 ml | shallow (2") (media depth = 1") | strat media | 755 |
| 4 (control) | 600 ml | deep (4") | strat media | 863 |
| 5 | 900 ml | deep (4") | strat media | 794 |
| 6 | 1200 ml | deep (4") | strat media | 843 |
| 7 | 600 ml | shallow (2") | dev media | 612 |
| 8 | 900 ml | shallow (2") | dev media | 821 |
| 9 | 1200 ml | shallow (2") | dev media | 803 |
| 10 | 600 ml | deep (4") | dev media | 757 |
| 11 | 900 ml | deep (4") | dev media | 843 |
| 12 | 1200 ml | deep (4") | dev media | 821 |

As shown above in TABLE 15, the development and stratification of embryos on Cambro boxes with higher amounts of media (900 ml and 1200 ml) showed statistically significant higher embryo yields than the control amount of media (600 ml). The estimated difference between these media volume treatments was about 140 embryos per box. In addition, the deep Cambro boxes (4") showed statistically significantly higher embryo yields than the shallow Cambro boxes (2"). The estimated difference between these two box-depth treatments was about 170 per box.

Osmolality Measurements: The osmolality of the media was measured after 12 weeks of incubation on development media. The development media had an initial osmolality of 336 mM/kg (10% PEG). The results are shown below in TABLE 16.

TABLE 16

CHANGE IN OSMOLALITY OF DEVELOPMENT MEDIA AFTER 12 WEEK DEVELOPMENT INCUBATION

| Treatment Condition | Osmolality (mM/kg) |
|---|---|
| control shallow cambro box (2") (600 ml) | 160 |
| shallow cambro box: 900 ml | 200 |
| shallow cambro box: 1200 ml | 220 |
| control deep cambro box (4") (600 ml) | 170 |
| deep cambro box: 900 ml | 190 |
| deep cambro box: 1200 ml | 210 |

Conclusion: As shown in TABLE 16, higher development media volumes maintained higher osmolalities after a 12 week incubation. However, with development media having an initial osmolality of 336 mM/kg, even with the additional media volume, none of the boxes maintained an osmolality higher than 250 mM after 12 weeks.

Germination Data

The effect, of media volume, box-depth and stratification treatment on the embryo germination frequency was analyzed using a generalized linear mixed model. The random effects in this model were batches and cambro-boxes within batches.

Category 1 Germinants:

Category 1 germination was assessed as described in Example 3.

TABLE 17

SHOWS THE ESTIMATED MEAN CATEGORY 1 GERMINATION FREQUENCY FOR EACH STRATIFICATION TREATMENT ALONG WITH 90% CONFIDENCE INTERVALS.

| Treatment Condition | Mean Germination frequency (cat 1) | Lower 90% CI | Upper 90% CI | Group |
|---|---|---|---|---|
| Stratification media (post-dev media change to strat media (w/o PEG) | 4.1% | 0.020 | 0.084 | A |
| Maintained on Dev media (+PEG) | 6.7% | 0.034 | 0.130 | B |

Treatment conditions shown in TABLE 17 with the same group level are not statistically significant at a 90% confidence level, whereas treatment conditions with different group letters are significantly different.

As shown above in TABLE 17, there was a significant difference in the frequency of category 1 germinants (p=0.007, confidence level 90%) resulting from embryos that were maintained on development media (+PEG) during stratification, in comparison to the frequency of category 1 germinants resulting from embryos that were transferred from development media to stratification media (no PEG), prior to stratification.

Category 3+2 Germinants were assessed as follows: a Category 1+2 germinant (bipolar) includes the following features: the presence of a 1 mm root (no nubbins) and the presence of epicotyl leaves (no size or number), that are visible to the eye.

TABLE 18

SHOWS THE ESTIMATED MEAN CATEGORY 1 GERMINATION
FREQUENCY FOR EACH STRATIFICATION TREATMENT
ALONG WITH 90% CONFIDENCE INTERVALS.

| Treatment Condition | Mean Germination frequency (cat 1) | Lower 90% CI | Upper 90% CI | Group |
|---|---|---|---|---|
| Stratification media (post-dev media change to strat media (w/o PEG) | 7.0% | 0.037 | 0.128 | A |
| Maintained on Dev media (+PEG) | 11.5% | 0.064 | 0.198 | B |

Treatment conditions shown in TABLE 18 with the same group level are not statistically significant at a 90% confidence level, whereas treatment conditions with different group letters are significantly different.

As shown above in TABLE 18, there was a significant difference in the frequency of category 1+2 germinants (p=0.002, confidence level 90%) resulting from embryos that were maintained on development media (+10% PEG, osmolality=336 mM/kg) during stratification, in comparison to the frequency of category 1+2 germinants resulting from embryos that were transferred from development media to stratification media (0.0% PEG, osmolality=120 mM/kg), prior to stratification.

Germination frequency was also assessed for category 1 and category 1+2 germinants resulting from embryos generated using treatments 1 to 6 as described in TABLE 12. The results of the statistical analysis of the differences observed in germination frequency are shown below in TABLE 19.

TABLE 19

STATISTICAL SIGNIFICANCE OF DIFFERENCES
IN GERMINATION OBSERVED USING VARIOUS
TREATMENT METHODS.

| Treatment Condition | DF | Difference observed in Cat 1 Germination freq. (p-value) | Difference observed in Cat 1 + 2 Germination freq. (p-value) |
|---|---|---|---|
| Media Volume (600 ml control v. 900 ml or 1200 ml) | 2 | 0.453 | 0.454 |
| Box Depth (shallow 2" v. deep 4") | 1 | 0.943 | 0.791 |
| Stratification media (post-dev media change to strat media (w/o PEG) v. maintained on dev media during stratification) | 1 | 0.007 | 0.002 |
| Media * Depth | 2 | 0.820 | 0.879 |
| Media * Strat | 2 | 0.424 | 0.654 |
| Depth * Strat | 1 | 0.348 | 0.340 |
| Media * Depth * Strat | 2 | 0.914 | 0.918 |

As shown above in TABLE 19, when analyzing the significance of the differences observed in germination frequency after embryo treatment with different media volumes, different box depths and different stratification media conditions, only the differences observed after different stratification media conditions were statistically significant. A statistically significant difference in stratification media conditions was observed both for the category 1 germinants (0.007) and for category 1+category 2 germinants (0.002).

This is an important result, indicating that the method of incubating embryos on development media with an initial osmolality of at least 300 mM/kg to 450, for a period of from 7 to 12 weeks, at room temperature, followed by stratifying the embryos on the same development media, i.e., transferring the embryos on development media to 0° C. to 10° C. for at least 1 week, results in increased embryo yield (as described in EXAMPLES 2-3), as well as increased embryo frequency, and improved vigor of germinants (as shown in EXAMPLE 2 and FIG. 2 (showing 13 of 15 genotypes in treatment 14 were observed to have more vigorous epicotyl, longer roots, or both). These results are in comparison to a control method that involved transferring embryos from development media (osmolality of at least 300 mM/kg) to stratification media (osmolality of 120 mM/kg), followed by stratification at 1° C. to 10° C. for at least 1 week.

Therefore, the method of maintaining the embryos on development media during stratification provides the unexpected advantage of increasing embryo yield and increasing germination frequency. The methods of the invention also provide the advantages of ease of manipulation of large numbers of embryos due to reduced number of steps, and ability to stratify and optionally store embryos in a post-development stage at 1° C. to 10° C. for up to 3 months to 6 months prior to germination.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for producing stratified cotyledonary conifer somatic embryos comprising:
    (a) incubating a culture comprising immature conifer somatic embryos in a culture vessel comprising a development medium comprising PEG at a concentration of from 1% to 15% and having an osmolality in the range of from 300 mM/Kg to 450 mM/Kg at a temperature of from 22° C. to 25° C. for a first incubation period sufficient in length for at least a portion of the embryos to reach anatomical maturity; and
    (b) subjecting the embryos in the culture vessel comprising the development medium comprisine PEG at a concentration of from 1% to 15% and having an osmolality in the range of from 300 mM/Kg to 450 mM/Kg, in accordance with step (a), to a temperature of from 0° C. to 10° C. for a second incubation period of at least one week to produce stratified cotyledonary somatic embryos.

2. The method of claim 1, wherein. the development media comprises PEG at a concentration of from about 7% to about 15%.

3. The method of claim 1, wherein the first incubation period is from 7 weeks to 12 weeks.

4. The method of claim 1, wherein the second incubation period is from 1 week to 8 weeks.

5. The method of claim 1, wherein the second incubation period is from 1 week to 6 months.

6. The method of claim 1, further comprising culturing the embryos treated in accordance with step (b) in or on a germination medium to produce germinants.

7. The method of claim 1, wherein the embryos in the first culture are singulated prior to the first incubation period.

* * * * *